United States Patent [19]
Lindekugel

[11] Patent Number: 6,152,732
[45] Date of Patent: Nov. 28, 2000

[54] FACEBOW WITH SIGHTING STRUCTURE

[75] Inventor: Eric Lindekugel, Fort Collins, Colo.

[73] Assignee: Water Pik, Inc., Fort Collins, Colo.

[21] Appl. No.: 09/364,764

[22] Filed: Jul. 30, 1999

[51] Int. Cl.$^7$ .................................................. A61C 19/04
[52] U.S. Cl. ............................................................. 433/73
[58] Field of Search .................................. 433/57, 68, 73

[56] References Cited

U.S. PATENT DOCUMENTS

| | | | |
|---|---|---|---|
| 3,084,438 | 4/1963 | Goodfriend | 433/73 |
| 3,224,096 | 12/1965 | Stuart . | |
| 4,084,319 | 4/1978 | Dragan . | |
| 4,252,524 | 2/1981 | Dragan . | |
| 4,261,696 | 4/1981 | Hobo | 433/73 |
| 4,616,998 | 10/1986 | Wong . | |
| 4,639,220 | 1/1987 | Nara et al. | 433/73 X |
| 4,695,252 | 9/1987 | Edwardson . | |
| 5,090,901 | 2/1992 | Levandoski . | |
| 5,385,470 | 1/1995 | Polz . | |
| 5,632,619 | 5/1997 | Polz . | |

FOREIGN PATENT DOCUMENTS

| | | |
|---|---|---|
| 0433732 | 11/1990 | European Pat. Off. . |
| 3540756 | 5/1987 | Germany . |
| 19636281 A1 | 3/1998 | Germany . |

OTHER PUBLICATIONS

Girrbach, rotofix®—Gesichtsbogen Instruction Pamphlet, available at least as early as Jul. 30, 1999.

Ivocar, Universal Transferbogen System UTS Operating Instructions, available at least as early as Jul. 30, 1999.

Jensen Industries Inc., Artex® Articulation System 1998/99 Models, available at least as early as Jul. 30, 1999.

Jensen Industries Inc., Artex® Articulation System Catalog, available at least as early as Jul. 30, 1999.

*Primary Examiner*—Nicholas D. Lucchesi
*Attorney, Agent, or Firm*—Dorsey & Whitney LLP

[57] ABSTRACT

A facebow having a sight structure, co-linearly moving arms, and ear pieces shaped to provide repeatable registration of the facebow on a patient's face. The facebow is able to be sterilized as a unit or can be partially disassembled for sterilization.

23 Claims, 10 Drawing Sheets

FACEBOW WITH SIGHTING STRUCTURE

FIELD OF THE INVENTION

This invention relates to a facebow for use in registering the position of a bite fork on a patient's face, and more particularly relates to a facebow having a unique sighting structure to allow convenient alignment of the facebow on the patient's face, along with a gear assembly creating co-linear arm movement, as well as ear pieces for securely positioning the facebow on the patient's face.

BACKGROUND OF THE INVENTION

A facebow is used in conjunction with a bite fork and transfer jig to orient the molds made of a person's upper and lower tooth structures on a dental articulator. The molds are positioned in an articulator for analysis of the person's bite. The facebow, transfer jig and bite fork help properly position the molds in the articulator to replicate the person's bite. The alignment of the bite fork in the person's mouth is important to insure the proper orientation of the molds in the dental articulator. The facebow helps properly orient the bite fork.

As is known in the art, the bite fork is adjustably attached to the transfer jig, and the transfer jig is fixed to the facebow. The first two reference points are created by the engagement of the facebow arms in the patient's ears. However, a vertical axis dimension, or third point of reference, must be used to thoroughly orient the models in the dental articulator. The facebow is aligned with the third point of reference by generally pivoting through a vertical arc in front of the patient's face to a particular position in alignment with the third reference point, and then fixing the bite fork to the transfer jig. This fixes the orientation of the bite fork in alignment with the third point of reference.

The third reference, or anterior reference point, is generally positioned by measuring 43 millimeters above the lateral incisor edge on the right, central or lateral incisors. The anterior reference point is generally positioned just underneath the right eye of the patient. The location of the reference point is typically noted by a mark, such as an ink mark, on the patients face.

To align the facebow with the third point of reference, the facebow is positioned on the patient's face, with the transfer jig attached to the facebow. The third point of reference is obtained by aligning the facebow with the anterior reference point on the patient's face. The facebow is moved through a vertical arc in front of the patient's face, pivoting about the engagement of the facebow with the patient's ears.

Typically, the facebow is properly positioned in alignment with the anterior reference point by using a reference pointer which swings inwardly from one of the facebow arms toward the patient's face. The end of the pointer is aligned with the reference point on the patient's face to properly position the facebow. Since the anterior reference point is generally just underneath the right eye of the patient, the patient can be disturbed by the movement of the pointer towards the anterior reference point for fear that the pointer will contact the patient's eye. This makes the procedure uncomfortable for the patient, and often results in inaccurate facebow placement since the patient frequently moves in response to the use of the pointer.

Dental professionals, due to these issues related to the use of the pointer, often do not use the pointer at all, but rather just position the facebow in the approximate position that the pointer would place it. This general positioning is not precise, and often leads to misalignment of the molds in the articulator.

Another issue with respect to existing facebows is that it is difficult to properly position the left and right arms for engagement with the patient's ears and at the same time keep the facebow centered on the patient's face. This is difficult since the arms on many presently available facebows move independently of one another. If the facebow is not perfectly centered on the patient's face, the alignment of the resulting molds in the articulator can be inaccurate. Even in available facebows where the arms do not move independently (where the arms must be made in left and right pairs), it is difficult to fix the position of the arms with respect to one another. Additionally, compass-type facebows cause the transfer jig to be misaligned forwardly or rearwardly with respect to the patient's face as the facebow arms are opened and closed.

A further issue with respect to existing facebows is the inaccurate engagement of the facebow with the patient's ears. Each arm of the presently-available facebow typically has an ear piece positioned at its tip to insert into the patient's ear canal. However, the existing ear pieces are difficult to repeatably position in a patient's ear to obtain a consistent engagement therein. In other words, the ear pieces can be positioned in a patient's ear in several different ways and result in several different alignments, one corresponding with each different plug positioning.

Finally, the sterilization of the existing facebows are often inconvenient in that the facebow either must be taken apart to fit into an autoclave, or because not all pieces of the facebow can withstand the autoclave process.

It is with the above limitations of the presently available facebows that the invention described and claimed herein was developed.

SUMMARY OF THE INVENTION

The instant invention relates to an improvement of current facebows by using a sight structure instead of a pointer to locate the third point of reference on a patient's face. The invention also addresses improvements by allowing either the entire facebow or the removable ear pieces to be steam, chemical vapor or cold sterilized. In addition, the ear pieces have been designed to be more anatomically correct, thus achieving a more stable and repeatable positioning in the patient's ear.

In the instant invention, the location of the arbitrary third point of reference is located by using a sight structure incorporated into the facebow assembly. This technology differs from the traditional means of either a pointer or a nasion (which fits in the notch of a person's nose, between his eyes).

The overall functions of the inventive facebow assembly involve opening and closing of the arms, locking of the arms, use of the sight or pointer to align with the third point of reference, and attachment of the transfer jig assembly. The arms open and close colinearly such that the anterior-posterior distance between the ear pieces and the main body remain constant, avoiding potential errors associated with a compass type of facebow. The arms are indirectly linked through a pinion gear and gear rack such that the body of the facebow is consistently centered between the left and right arms.

The arms are locked into position with respect to one another by a cam lock knob which is rotationally positioned between the two cover plates of the main body. The cam lock is designed so that no more than one-half turn is required to lock the arms in the fixed position. The main body of the facebow receives the transfer jig assembly in the manner similar to existing facebows, such as the Denar® Slidematic.

This manner utilizes a set screw to fasten the transfer jig in an aperture formed in the main body.

The most significant improvements to the facebow design are the sight, the autoclavability, the anatomical ear pieces, and the arm movement. The use of the sight eases the facebow measurement procedure and decreases the amount of time required of other devices by allowing the practitioner to quickly home in on the arbitrary third point of reference, which was previously located via the use of a pointer.

The use of the sight, while not always as accurate as the use of the pointer, can be used to position the facebow more accurately and repeatably than simply guessing such as is done when the pointer is not used.

The two key features of the sight structure are the size of the gap and the angle with respect to the main body of the facebow. These features help assure proper alignment of the facebow with the third reference point. Based on a common anatomical assumption that the front of the face is approximately 3.25 inches from the external auditory meatus, it has been determined that a gap of 0.040 inches (forty thousandths of an inch) at an angle of 7.5 degrees gives an approximate tolerance of plus or minus two degrees from level. It should be noted that the reason the facebow should be level with respect to the head is because the current Denar indirect transfer mount system relies on this to accurately place the cast model in an articulator. This is important for retrofit capabilities.

In detail, the invention pertains to a facebow for registering the position of a third reference point on a patient's face, the facebow comprising a left arm, a right arm, a main body adjustably receiving the left and right arms, and a sight structure formed on the housing for use in locating the third reference point.

The invention also pertains to a method of using a facebow on a patient's face, including ears, having a reference point thereon, to properly orient a bite fork, adjustably engaged with the facebow, with respect to the patient's face, the method including the steps of providing a main body and left and right arms on the facebow and engaging the left and right arms with the respective ears of the patient, providing a sight structure on the facebow and viewing the patient's face through the sight to locate the reference point; and securing the main body to the bite fork to register the relative position of the bite fork to the facebow.

Further, the instant invention also addresses a rack and pinion assembly for a facebow, including a rack and pinion assembly positioned in the main body and operably engaging the left and right arms to cause the right arm and the left arm to move in opposite directions from one another upon movement of one arm, respectively. The rack and pinion assembly includes a rack attached to each arm, one of the racks facing downwardly, and one of the racks facing upwardly, the racks facing each other; a pinion gear rotatably fixed in the main body on a horizontal axis of rotation and engaging both of the racks; wherein movement of one of the left and right arms with respect to the main body causes the other of the left and right arms to move in the opposite direction.

Additionally, the instant invention pertains also to an ear piece for use on a facebow having an arm, the ear piece including a body portion having a front side, a back side, a terminal end and a receiving end; a slot formed in the back side for receiving the arm; the front face at the terminal end forming a bulbous lobe.

The foregoing and other features, utilities and advantages of the invention will be apparent from the following more particular description of a preferred embodiment of the invention as illustrated in the accompanying drawings.

DETAILED DESCRIPTION OF THE PREFERRED EMBODIMENT

An arbitrary facebow is used to establish a relationship between the maxillary arch and the cranium, and then transfer that relationship to an articulator so a cast model of the patient's teeth can be positioned in an articulator in the same relationship. It is considered an arbitrary facebow because rather than locating on the kinematic hinge axis, it locates in the auditory meatus of each ear (the first two reference points) and assumes the kinematic axis is 12 millimeters anterior (forward), and five millimeters inferior (downward). The third point of reference in this system is located with a reference plane locator and is generally indicated by a mark made on a patient's face 43 millimeters above the incisor edge, as described above. When the facebow is aligned with the third point of reference, the result places the cast models in the middle of the articulator. Preferably, the above facebow is used with a transfer jig and articulator made by Denar®, but can be modified by anyone of ordinary skill in the art to work with other types of articulators. While the device described herein is referred to as a facebow, it is also known as an earbow or measuring bow, which are all used for generally the same purpose.

Figure 1:
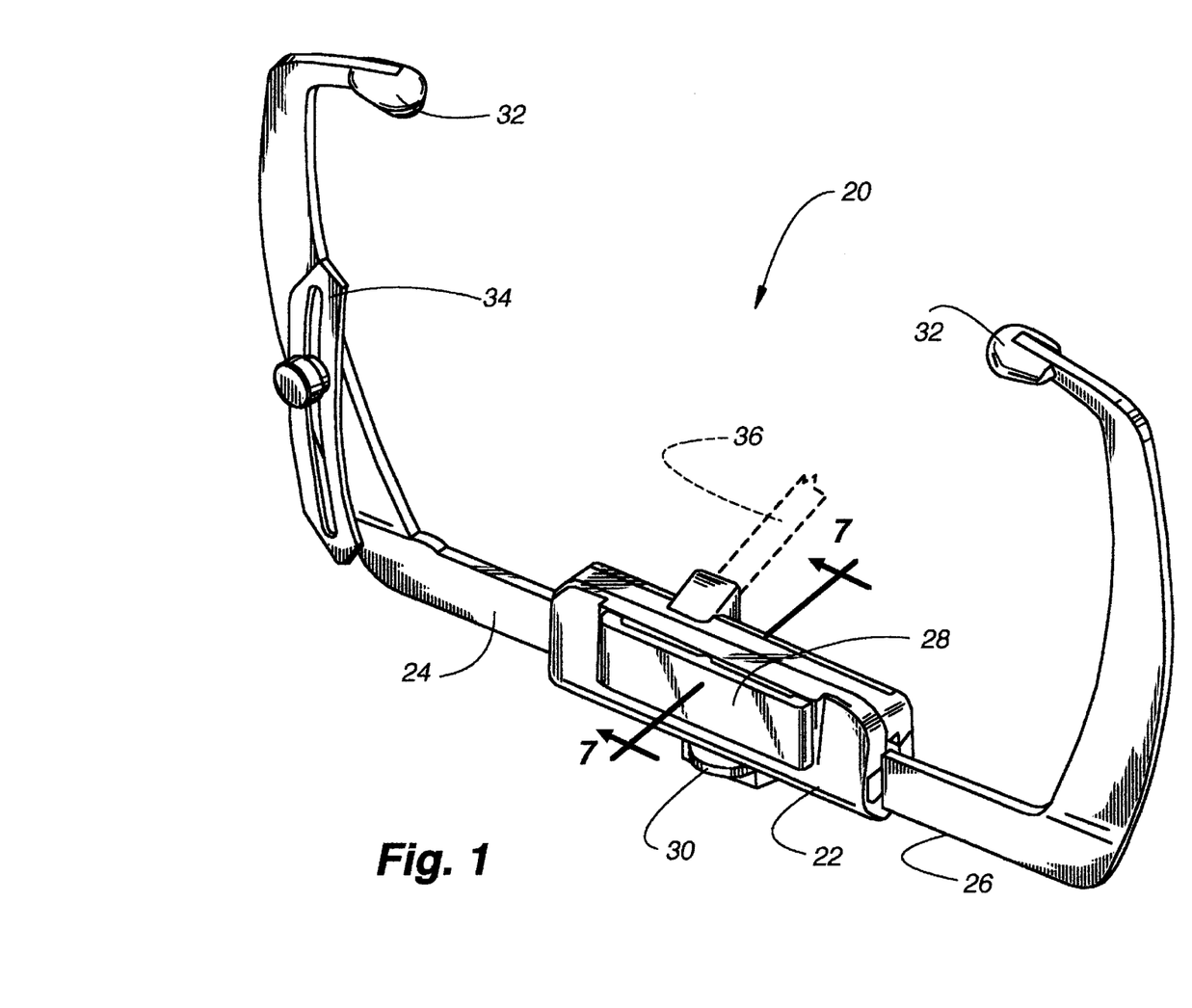
FIG. 1 shows the facebow of the present invention including the sight structure, the left and right arms, and the left and right ear pieces.

Referring first to FIG. 1, the facebow 20 of the present invention is shown including a main body 22 from which extends left 24 and right 26 arms, a site structure 28 on the top of the main body, a cam lock knob 30 on the rear of the main body for locking the position of the left and right arms in a fixed position with respect to the main body, and an ear piece 32 at the end of each of the left and right arms. The left 24 and right 26 arms move co-linearly with respect to the main body 22 to keep the main body in a centered position with respect to the left and right arms. A pointer structure 34 is attached to the left arm 24 as an alternative to using the site structure for locating the third arbitrary point on the patient's face.

The main body 22 includes a keyed recess for receiving the top end of a rod 36, which is a part of a jig assembly, connecting the bite fork with the facebow as is known in the art. The keyed recess can have a D-shape to allow the receipt of a jig assembly in one orientation only. A set screw is used to fix the transfer jig in the main body (not shown).

As previously mentioned, the facebow 20 is used to properly orient the bite fork, positioned in the patient's mouth, on the patient's face with respect to generally fixed structures on the patient's face. Obtaining the proper orientation requires the insertion of the ear pieces 32 into the patient's ears, and lining up the position of the main body 22 of the facebow along a certain vertical height in alignment with the third arbitrary point 40 marked on the patient's face. Once the proper position is found, the left 24 and right 26 arms are locked in position, and the bite fork is affixed to the jig, which is affixed to the main body of the facebow, thus allowing the translation of the proper orientation on the person's face to the dental articulator.

Figure 2:
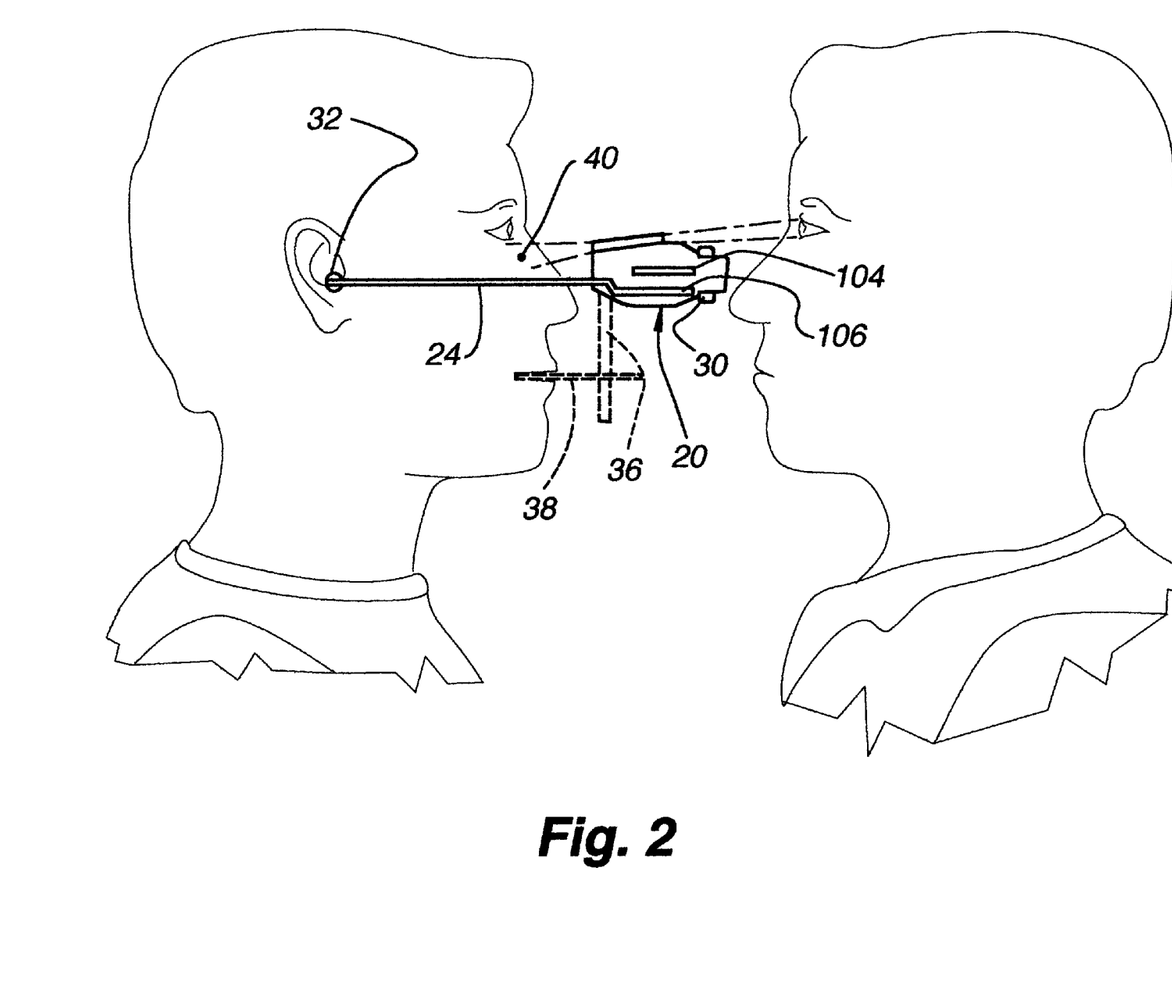
FIG. 2 is a schematic view of the facebow of the present invention being used to register the position of the bite fork on the patient's face.

FIG. 2 shows the use of the facebow 20 of the present invention with the ear pieces 32 inserted into respective ear of the patient (only the right side is shown in FIG. 2) with the bite fork 38 positioned in the patient's mouth and slidably connected to the jig, with the top end of rod 36 of the jig inserted into the keyed aperture formed in the main body 22. The dental professional aligns the facebow 20 in the proper vertical orientation by viewing the patient's face through the sight structure and locating the mark 40 representing the third reference point on the patient's face. The mark 40 is positioned in the sight structure centered from top to bottom in the gap in the sight structure. The arms 24 and 26 are fixed in position with the main body 22, and the facebow 20 and jig are fixed together.

Figure 3:
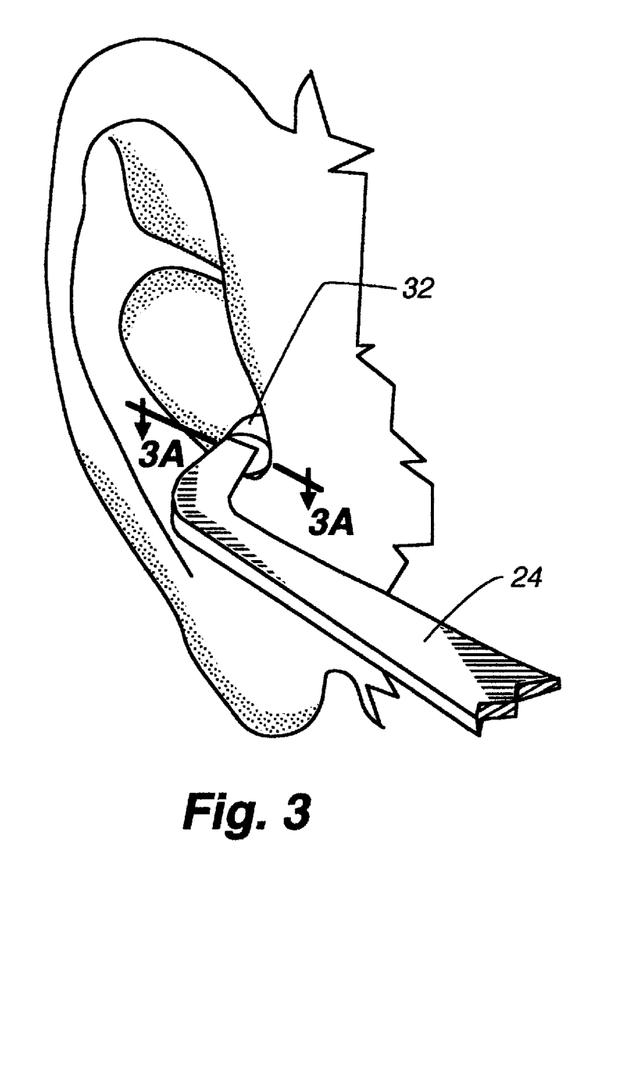
FIG. 3 is a partial view of the left arm showing the tip of the left arm positioned in the ear canal of a patient.
Figure 3A:
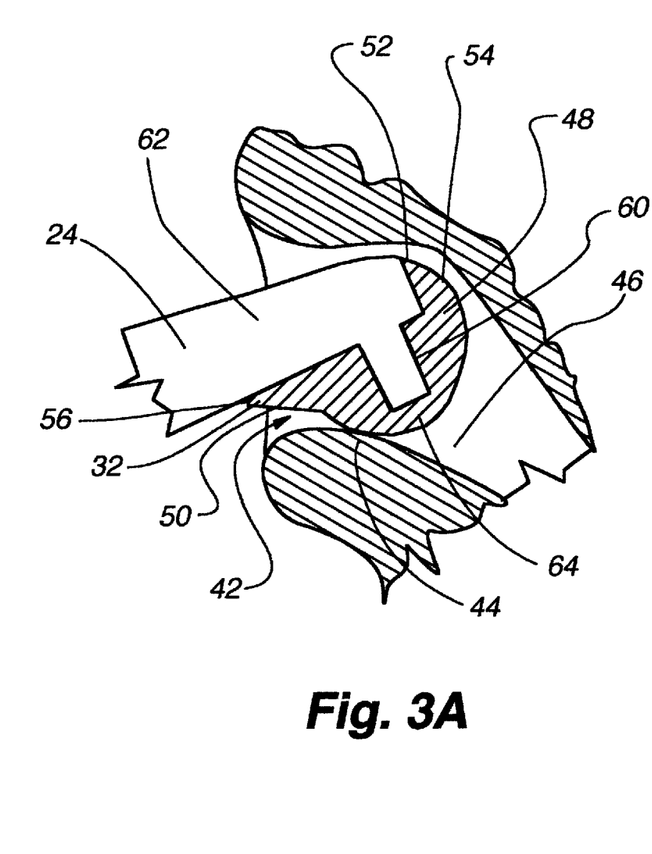
FIG. 3A is a section taken along the line 3A—3A of FIG. 3, and shows the front lobe of the ear piece engaging the front portion of the ear canal.

FIGS. 3 and 3A show the inventive ear piece 32 as it is attached to the ends of each facebow arm, and upon insertion into the ear. The shape of the ear piece 32 is important to provide repeatable and secure positioning of the facebow arms with the respect ear canal. Previously available ear pieces were typically conical in shape and fit loosely in the patient's ear, requiring the dental professional to pull the facebow away from the patient's face to seat the ear pieces securely against the front of the ear for proper registration of the ear pieces in the ear. This loose positioning sometimes created an error in the final orientation of the bite fork with respect to the patient's head structure. The process was also not very repeatable.

The ear pieces of the present invention are designed for both patient comfort and stability of measurement. This is accomplished by creating a rounded "hook" like feature 42, the intent of which is to allow the ear piece 32 to contact the anterior portion 44 of the ear canal 46, hence creating a snug fit and a positive, repeatable, registration. Preferably, the material used to construct the ear pieces is a thermoplastic elastomer, such as Santoprene, that has a relatively soft durometer measurement, such as approximately 80 shore A. Santoprene can withstand many types of disinfecting processes including steam autoclaving, chemical vapor autoclaving, and cold sterilization. The ear piece 32 thus is more comfortable, easier to sterilize, and provides a more stable positioning. The thermoplastic elastomer material also dampens noise vibrations normally transferred to the ear during the procedure, this noise being much more easily transferable through typical metallic ear pieces, or ear pieces made of harder material than the thermoplastic elastomer.

Each ear piece 32 defines a body portion 48 having a front side 50, a back side 52, a terminal end 54 and a receiving end 56. A slot 58 (FIG. 4) is defined along its back side 52, and a recess 60 is formed in communication with the slot to receive the similarly shaped end 62 of the facebow arm. This allows the ear piece 32 to be securely positioned on the facebow arm 24 (or 26) and easily removed from the facebow arm. The front side 50 and terminal end 54 of the ear piece 32 define a bulbous shape 64 offset forwardly of the end 62 of the facebow arm (the "hook 42"), transitioning to a conical shape at the receiving end 56 of the ear piece 32. This bulbous lobe 64 extending forwardly from the facebow arm 24 positively engages the front structure 44 of the ear inside the ear canal 46 for a firm registration of the position of the facebow arm in the ear. See FIGS. 3 and 3A. There is no need to pull the facebow away from the patient's face after the ear pieces are inserted into the ear in order to obtain a positive engagement of the ear pieces within the ear given the new structure.

This new structure has also been found to be more comfortable than the generally conical shaped ear pieces. The effect of having a more convenient positive registration of the ear piece within the patient's ear is that the dental professional can more quickly and accurately position the facebow with respect to the patient's head, which ends up creating a more reliable positioning of the bite fork.

Figure 5A:
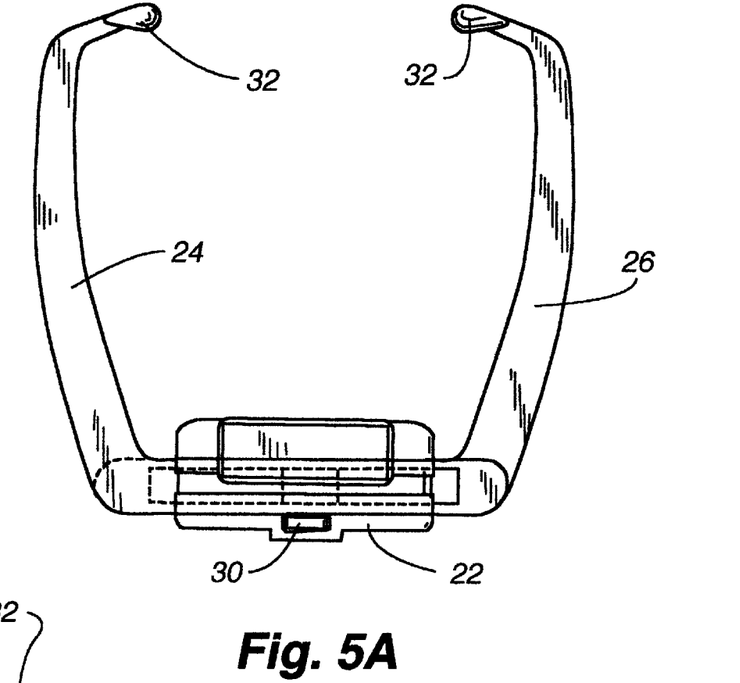
FIG. 5A is a top view of the facebow of the present invention showing the arms in the contracted position.
Figure 5B:
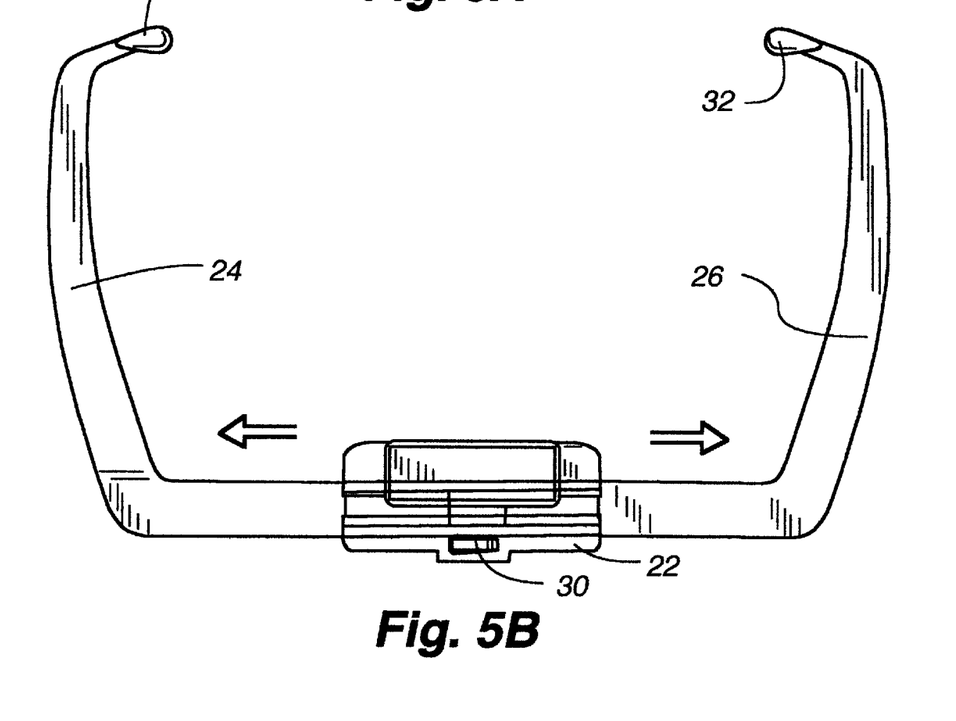
FIG. 5B is a top view of the facebow of the present invention showing the left and right arms in the extended position.

The movement of the facebow arms 24 and 26 with respect to the main body 22 is shown in FIGS. 5A and 5B. FIG. 5A shows the facebow 20 with the arms 24, 26 in the most contracted position. FIG. 5B shows the arms 24, 26 in the most extended position. Both of the arms 24, 26 can be moved with respect to the main body 22 by causing only one of the facebow arms to move. The other facebow arm will move proportionally in a co-linearly opposite direction, while keeping the main body centered between the arms. A rack and pinion gear system is positioned in the main body 22 and interacts with each of the facebow arms and the main body. The rack and pinion gear system allows the movement of one arm to cause the other arm to move in an opposite direction while keeping the main body centered between the arms. The centering of the main body between the arms is important for the proper orientation and registration of the position of the facebow on the patient's face and head, and thus the bite fork.

Figures 4, 4A:
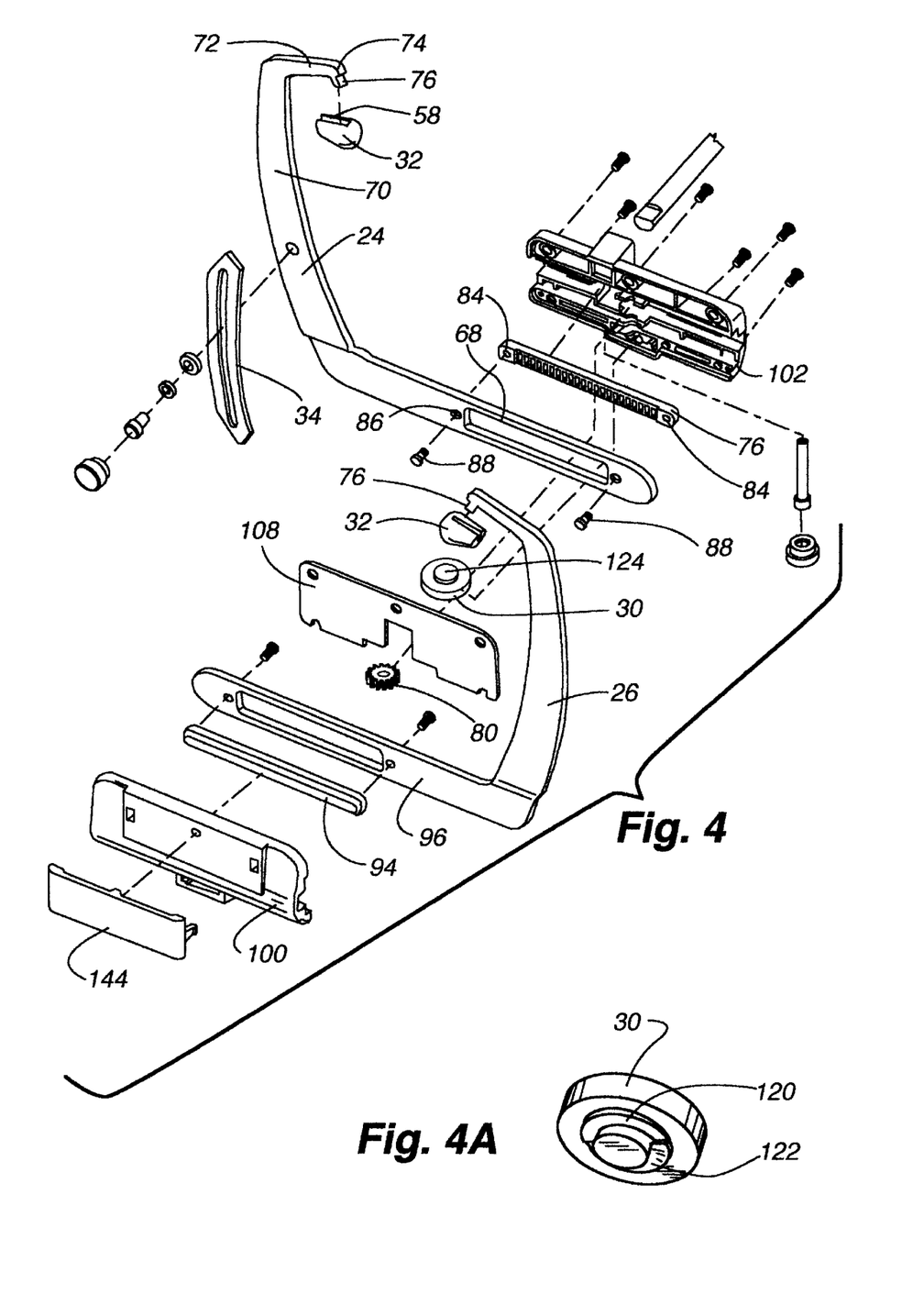
FIG. 4 is an exploded view of the facebow of the present invention.
FIG. 4A is an enlarged view of the opposite side of the cam lock as shown in FIG. 4.
Figure 6A:
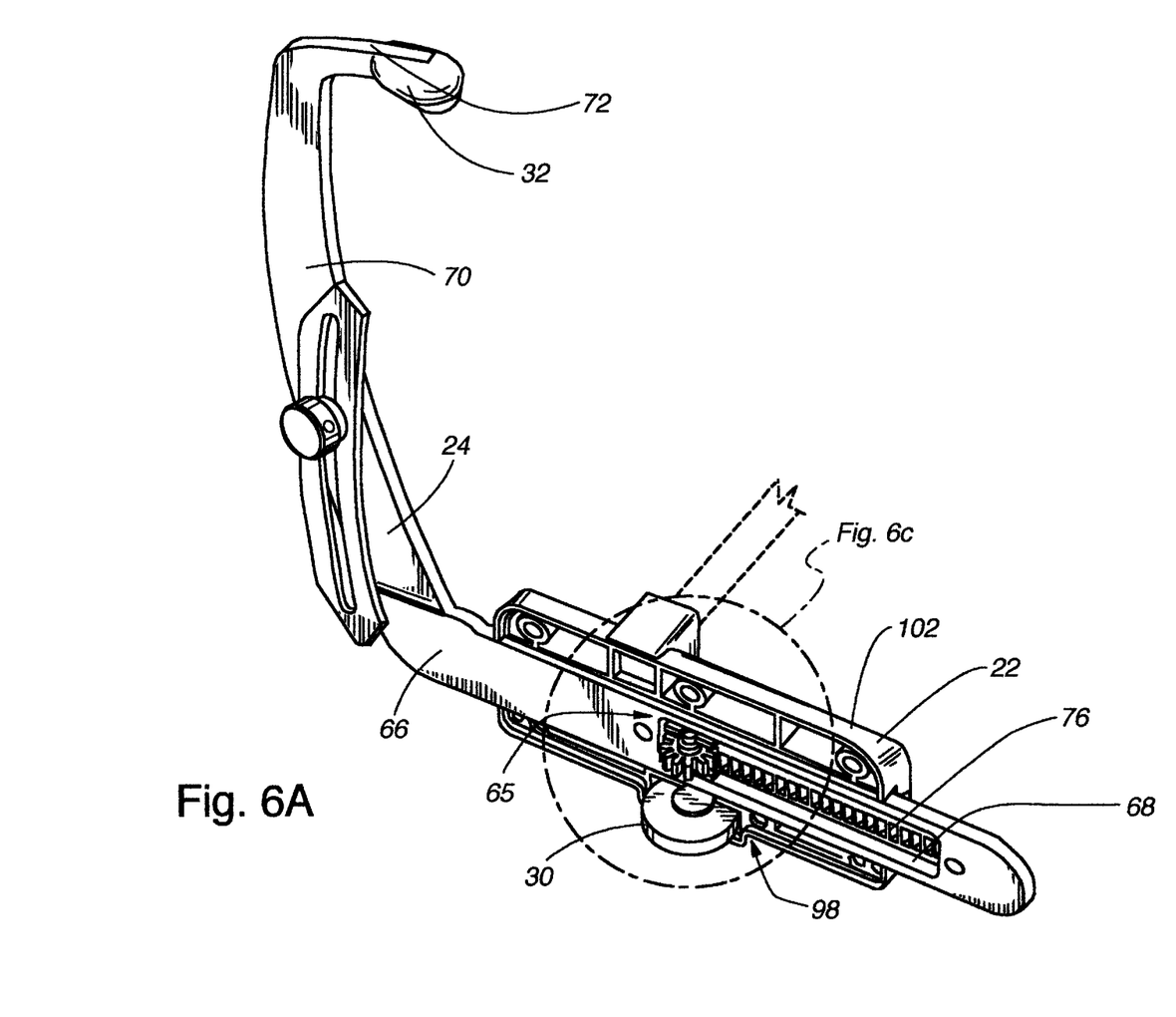
FIG. 6A is a partial view of the facebow of the present invention showing the top portion of the main body removed to expose the pinion gear rotatably mounted in the main body, and the rack of the left arm in engagement with the pinion gear, with the arm in the contracted position.
Figure 6B:
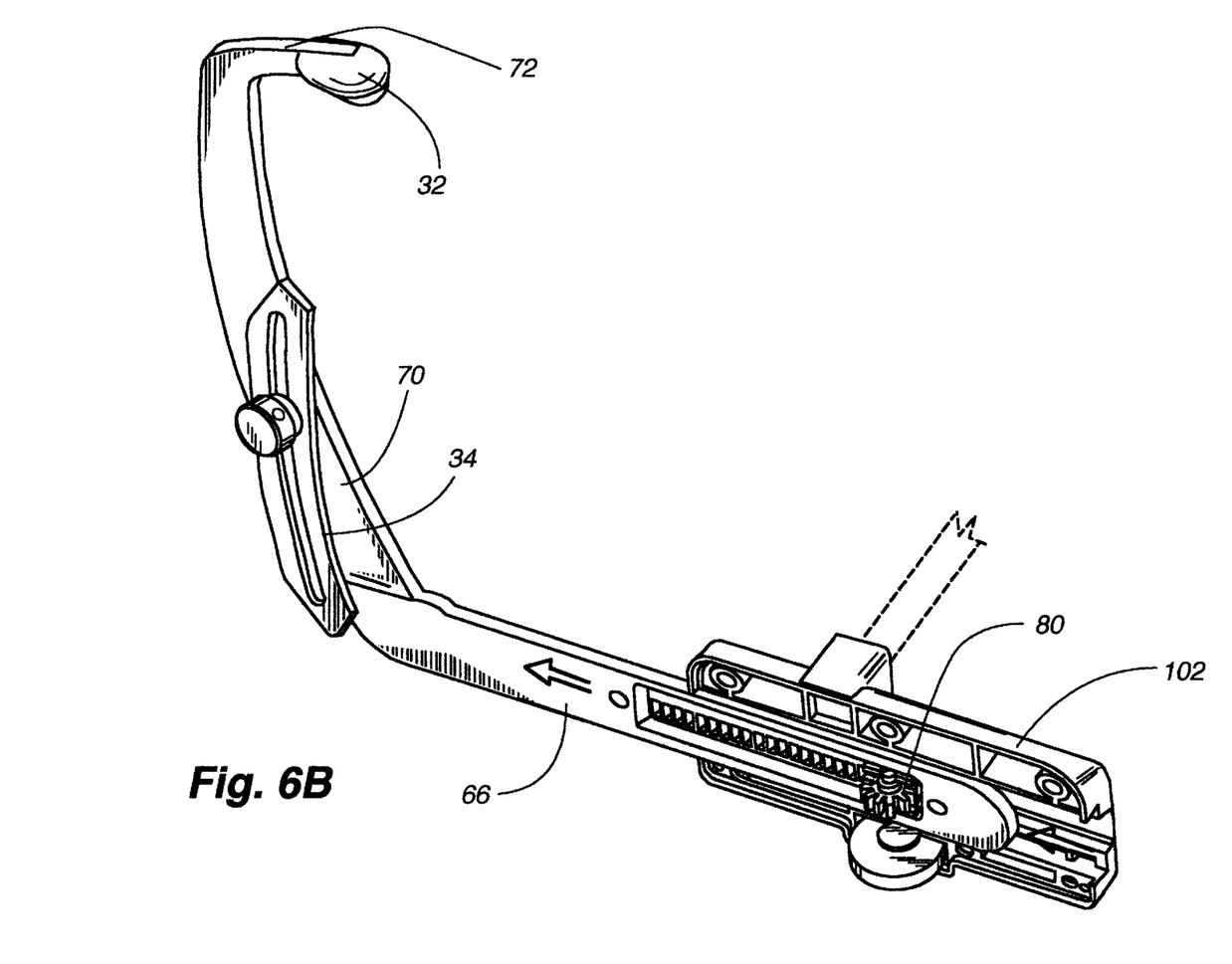
FIG. 6B shows the facebow of the present invention similar to 6A, with the left arm in the extended position.
Figure 6C:
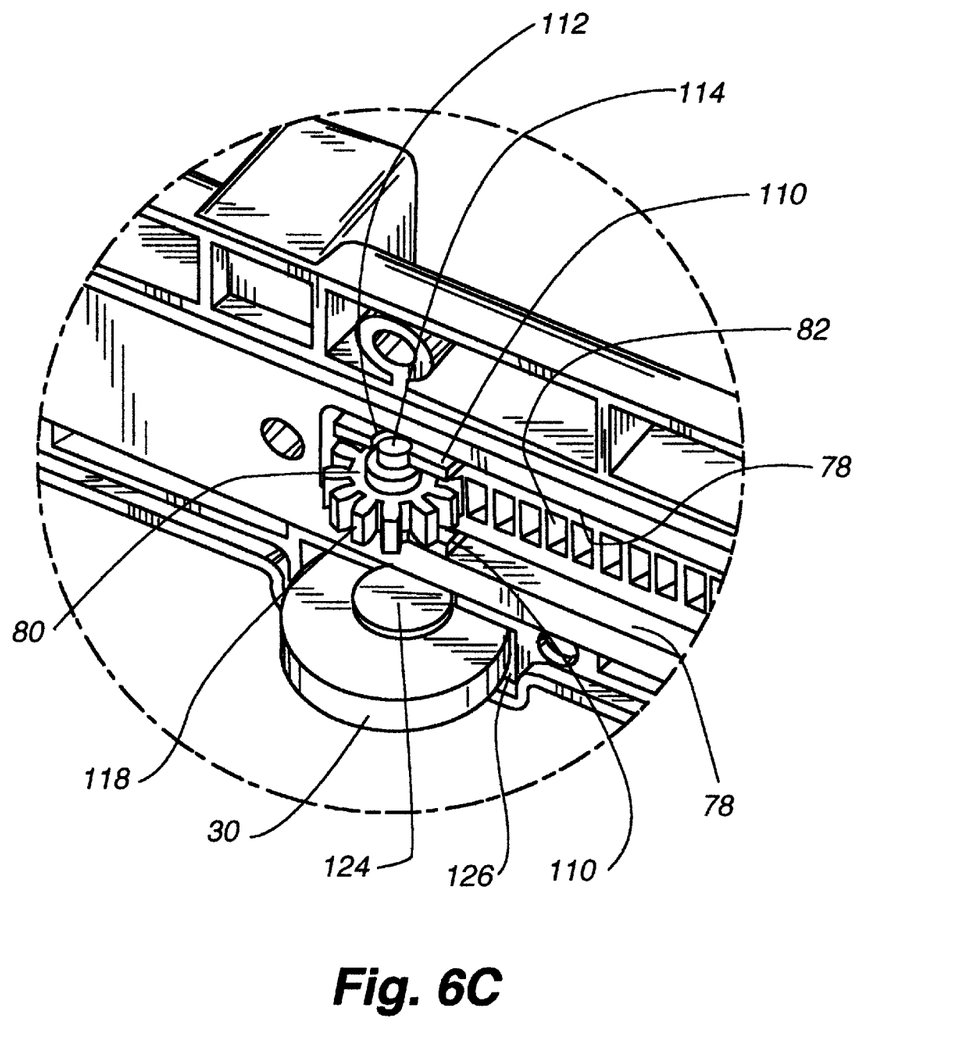
FIG. 6C is an enlarged view of the pinion gear rotatably positioned in the main body by a pair of yoke members, with the rack in engagement with the pinion gear.
Figures 7, 7A, 7B:
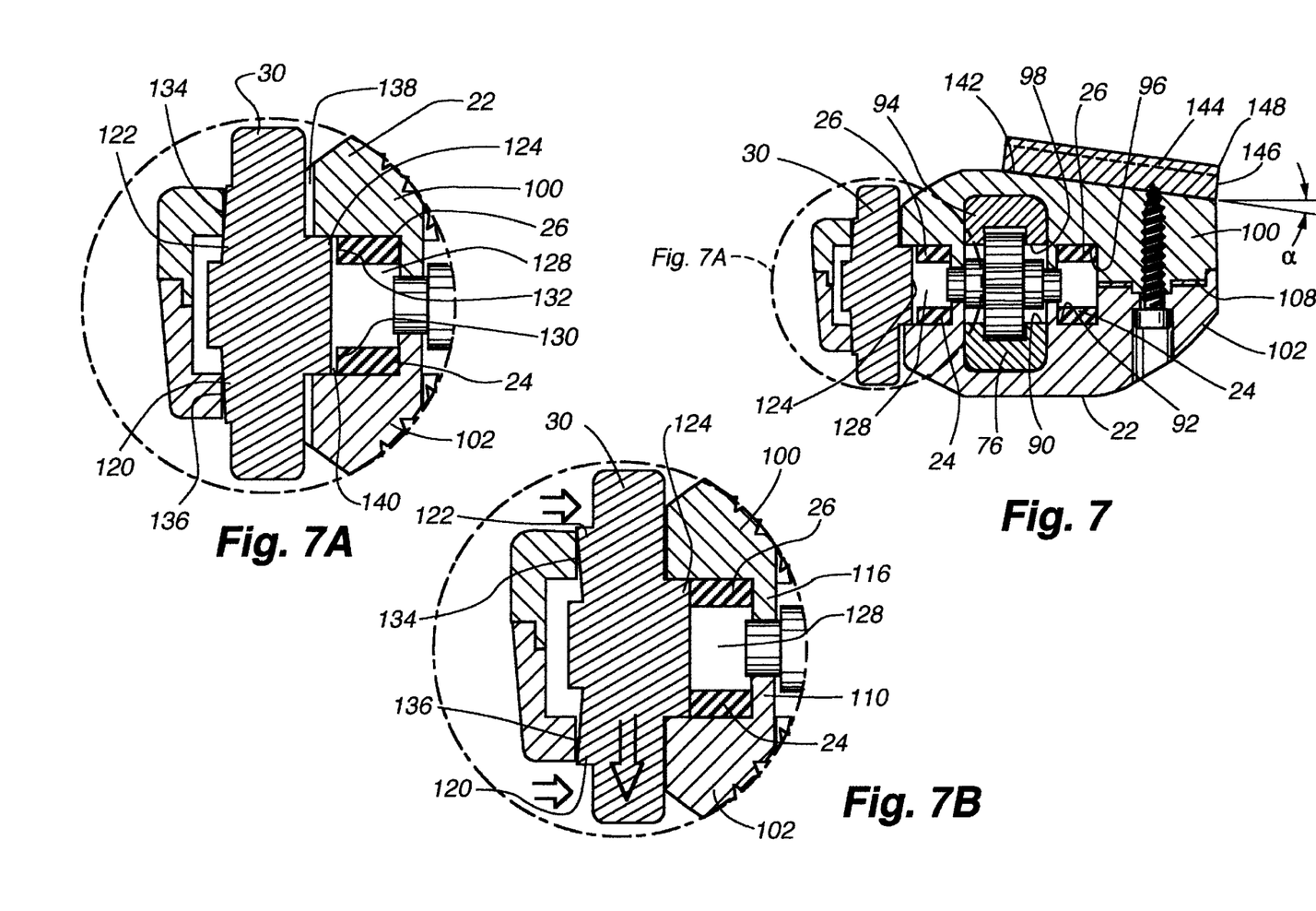
FIG. 7 is a section taken through line 7—7 of FIG. 1, and shows the cam lock in the disengaged position to allow the arms to move from the contracted to extended position as needed.
FIG. 7A is an enlarged view of a portion of FIG. 7, showing more detail of the cam lock knob in the disengaged position.
FIG. 7B is an enlarged section similar to FIG. 7A, showing the cam lock knob in the engaged position to fix the position of the facebow arms.

The rack and pinion structure 65 is shown in detail in FIGS. 6A, 6B, and 6C as well as FIGS. 4 and 7. Referring first to FIG. 6A, the left facebow arm 24 is shown. The right facebow arm is the same as the left facebow arm except it is used upside down. The left facebow arm 24 has generally a J-shape, with a first section 66 extending through the main body 22. In general, the first section defines a slot 68 and extends parallel to the plane of the patient's face when the facebow 20 is positioned on the patient's head. The second section 70 of the facebow arm extends at generally right angles to the first section. The second section 70 can also support the moveable pointer 34, as is known in the art. The third section 72 extends at a substantially obtuse angle to the second section 70, and receives the ear piece 32. The right facebow arm 26 has identical sections.

The terminal end 74 of the third section 72 (see FIG. 4) of the left facebow arm defines a tab 76 extending at right angles to the third section 72. The tab 76 is formed to be received in the recess 60 formed in the ear piece 32 to help securely attach the ear piece 32 to the third section 72 of the facebow arm 24, while at the same time allowing the ear piece 32 to be removed therefrom. The ear piece 32 surrounds the third section 72, except for the back surface of the third section, which is left exposed. Preferably, the back surface 52 of the ear piece 32 is flush with the back surface of the third section 72 of the arm 24 (see FIG. 3A). This is to maximize the distance the ear piece can extend in front of the third section for the positive registration of the ear piece within the ear as described above. The ear piece 32 is attached to the right arm 26 in the same manner.

The slot 68 formed in the first section of the left facebow arm 24 receives a gear rack 76. The gear rack 76 is centered along the width of the slot 68 to form a gap 78 between the longitudinal edges of the rack 76 and the longitudinal edges of the slot 68. These two parallel gaps 78 are important for the support of the pinion gear 80, as described below.

The gear rack 76, as shown in FIGS. 4 and 6A, B and C, is an elongated member having gear teeth 82 formed in one side. An aperture 84 is formed at either end of the gear rack 76 to correspond with the aperture 86 formed at each of the opposite ends of the slot 68 on the first section 66 of the arm 24. A fastener 88 is used to attach the rack 76 to the arm 24 through these corresponding apertures. The top plane 90 of the gear rack 76 is flush with the bottom surface 92 of the left facebow arm 24, as shown in FIG. 7.

The right facebow arm 26 is identical in structure to the left facebow arm 24. It is simply used upside down to form the right arm 26. It can include the optional pointer mechanism. The gear rack 94 is attached to the top side 96 of the right facebow arm 26 with the bottom surface 98 of the gear rack 94 being flush with the top surface 96 of the right facebow arm 26, as shown in FIG. 7. Each arm 24 and 26 has an offset formed in the second section (see FIG. 4) to place the second and third sections in the same plane for accurate measurements. The left arm is offset up (see FIG. 2) and the right arm is offset down (see FIG. 4).

The rack and pinion gear system 98 is formed in the main body 22 to include the left 24 and right 26 facebow arms and the main body 22. The main body 22 has a top portion 100 and a bottom portion 102, the bottom portion 102 being shown in FIG. 6A, 6B and 6C. The top 100 and bottom 102 portions of the main body 22 when positioned together (see FIG. 1) form two slots, top 104 and bottom 106, positioned vertically coextensive with one another and extending through the main body 22 from one end to the other. The first sections 66 of both the left 24 and right 26 facebow arms are each received in one of the slots. As shown in the drawings, the left arm 24 is positioned in the bottom slot 106 and the right arm 26 is positioned in the top slot 104. The bearing plate 108 (FIGS. 4 and 7) separates the two slots 104 and 106 along much of their length, as described below. Along the middle of the bottom slot 106 through the main body 22, a pair of yoke arms 110 extend into the slot 106, each of the arms 110 having a semi-circular notch 112 at its top end for receiving the axle 114 of the pinion gear 80. Each of the yoke arms 110 extends through the corresponding gap 78 between the gear rack 76 and the side wall of the slot 68 in the left arm 24 so that the yoke 110 can support the pinion gear 80, while allowing the left facebow arm 24 to slide through the main body 22 from one end of the slot 68 to the other end of the slot formed in the facebow arm 24. A corresponding yoke 116 is formed in the top slot 104, in the top portion 100 of the main body 22 and extends through the slot formed between the rack 94 and the side wall of the slot (not shown) formed in the right facebow arm 26 so that when the top 100 and bottom 102 portions of the main body 22 are attached together the axle 114 of the pinion gear 80 is rotatably restrained between the yoke arms 110 and 116. See FIG. 7.

The pinion gear 80 rests in the yoke arms 110 and 116. The pinion gear 80 is generally disk shaped with radially extending gear teeth 118 and an axle 114 extending from each side of the disk. Each axle extension is received in the yokes 110 and 116 as described above to allow the pinion gear 80 to rotate in place. When the pinion gear 80 is positioned in the yokes, the gear teeth 118 of the pinion gear 80 mesh with the gear teeth 82 in the bottom rack 76 as well as the gear teeth in the top rack 94. See FIGS. 6C and 7A.

In the assembled state, there is a cavity between the bottom surface 98 of the top rack 94 to the top surface 90 of the bottom rack 76, this cavity being approximately the thickness of the left 24 and right 26 facebow arms additively, the diameter of the axle extension 114 from the pinion gear 80, the thickness of the bearing plate 108 (described later), and the amount the yoke members extend above the slot formed through the upper and lower portions of the main body. See FIG. 7.

The rack and pinion system 98 as described allows the movement of one arm to cause the movement of the other arm. For instance, if the left facebow arm 24 is moved from the contracted position to the extended position, the movement of the arm 24 with respect to the pinion gear 80 causes the pinion gear to rotate. Because the pinion gear is also engaged with the rack 94 on the right arm 26, the pinion gear 80, as driven by the bottom rack 76, engages the top rack 94 to move the right facebow arm 26 opposite the left facebow arm 24. Because the pinion gear teeth positively engage both the top and bottom racks, the alignment of the left facebow arm 24 with the right facebow arm 26 is approximately constant, meaning that if the left facebow arm 24 is moved outwardly one inch, the right facebow arm 26 is moved outwardly one inch.

The bearing plate 108 is mounted in the main body 22 between the first 100 and second 102 sections to create a low friction surface upon which the left 24 and right 26 arms slide when being moved inwardly and outwardly. The bearing plate 108 also delineates the top 104 and bottom 106 slots along much of their lengths. The bearing plate 108 is relatively thin, approximately 0.31 inches in thickness, and is shaped (having cut-outs) so as to not interfere with the movement of the pinion gear 80 or the cam lock knob 30. The bearing plate 108 is made of PTFE (Teflon®), which eliminates the need for lubrication of the gear system. This rack and pinion gear system 98 is advantageous in that the racks 76 and 94 are assembled to fit to either of the facebow arms. Also, since the racks face upwardly and downwardly to oppose one another, the pinion gear 80 is more easily and securely positioned in the main body when assembled.

Previous rack and pinion gear systems in facebows had the gear teeth stamped along the front edge and corresponding rear edge of the facebow arms, with the pinion gear oriented to rotate around a vertical axis. The stamping of the gear teeth in the metal arms was relatively expensive, required separate processes for left and right arms, and the alignment of the vertically oriented pinion gear with the stamped gear teeth made the facebow more difficult and thus expensive to manufacture. In the current pinion gear system, the formation of the slot having the gear rack assembled thereon is much more efficient, and thus less expensive. In addition, if the gear rack 76 or 94 is damaged, the entire facebow arm does not need to be replaced, only the gear rack. Further, each arm is identical so there is no need to manufacture left and right arms separately.

Once the left 24 and right 26 arms of the facebow are properly positioned in the patient's ears, the position of the arms with respect to the main body must be fixed for an accurate measurement. In the present invention, the cam lock knob 30 as shown in FIGS. 4, 4A, 6A, 6B, 6C, 7A and 7B is used for this purpose. The cam lock knob 30 has a substantially cylindrical disk shape with one outer surface defining two circumferential cam surfaces 120 and 122 (see FIG. 4A), and the other side surface of the cam lock 30 knob defining a cylindrical protrusion 124. The cam lock knob 30 is housed in a recess 126 formed in the rear edge of the main body. The knob recess 126 is formed by both the top 100 and bottom 102 portions of the main body 22 when joined together. The cam lock knob 30 is actuated to engage the rear sides of each of the left 24 and right 26 facebow arms to fix the facebow arms in relative position to one another in the main body. The cam lock knob 30 is actuated by rotating the cam lock knob with respect to the main body 22.

FIGS. 7, 7A and 7B show this use of the cam lock knob 30 in detail. FIG. 7 shows the cam lock knob 30 positioned in the recess with the circular protrusion 124 extending into a cavity 128 formed by the combination of the upper 100 and lower 102 portions of the main body when connected together. The rear longitudinal edges 130 and 132, respectively, of the left and right facebow arms are exposed in the cavity 128 also. The cylindrical protrusion 124, which can be solid or an annular collar, can move inside the cavity 128 both axially and in rotation as described below. The outer surface of the cam lock knob 30, specifically the cam surfaces 120 and 122, engage a corresponding upper 134 and lower 136 surface of the main body 22. These surfaces are preferably corresponding cam surfaces.

FIGS. 7 and 7A show the cam lock knob 30 in the disengaged position, with the cam surfaces 120 and 122 on the outer side of the cam lock knob 30 engaging the housing at their thinnest position. In this position, a gap 138 is created between the inner surface of the cam lock knob 30 and the housing 22, and most importantly, a gap 140 is formed between the innermost surface of the cylindrical protrusion 124 and the rear edges 132 and 130 of the right 26 and left 24 (top and bottom), respectively, facebow arms. In this disengaged position, the left 24 and right 26 facebow arms can be moved inwardly and outwardly without interference.

The facebow arms 24 and 26 are fixed in the desired position by actuating the cam lock knob 30. FIG. 7b shows the cam lock knob 30 in the engaged position. The cam lock knob 30 is rotated to cause the cam surfaces 122 and 120 on the outer side surface of the cam lock knob 30 to engage the corresponding top 134 and bottom 136 surfaces of the housing 22 to force the cam lock knob 30 axially towards the facebow arms 24 and 26. This causes the cylindrical protrusion 124 on the inner surface of the cam lock knob 30 to engage the exposed rear edges 130 and 132 of the left 24 and right 26 facebow arms and thus fix their position by a clamping engagement. As shown, turning the cam lock knob 30 approximately one-half of one rotation causes the engagement of the cylindrical protrusion with the left and right facebow arms to fix their position. The cam surfaces 120 and 122 are designed to engage the facebow arms and fix their position when the cam lock knob 30 is rotated clockwise when viewed from the side having the cam surfaces. It is contemplated that the cam surfaces can also be formed to fix the position of the arms when the cam lock knob is rotated counter-clockwise.

In addition, while preferably the cam lock knob 30 is rotated only one-half of one turn to engage the facebow arms 24 and 26, the cam surfaces can be designed to require less or more turning of the knob 30 to effect engagement with the facebow arms. The left 24 and right 26 facebow arms are restricted from moving away from the cam lock knob 30 when engaged by the cam lock knob by the main body housing 22. The use of the cam lock knob 30 to fix the position of the left and right facebow arms with respect to the main body 22 is very convenient for the dental professional operating the facebow 20. The cam lock knob 30 is centrally positioned on the rear side of the main body 22, and can be accessed from the top side or bottom side, or both, of the main body 22 for quick and convenient operation.

Figures 8, 8A:
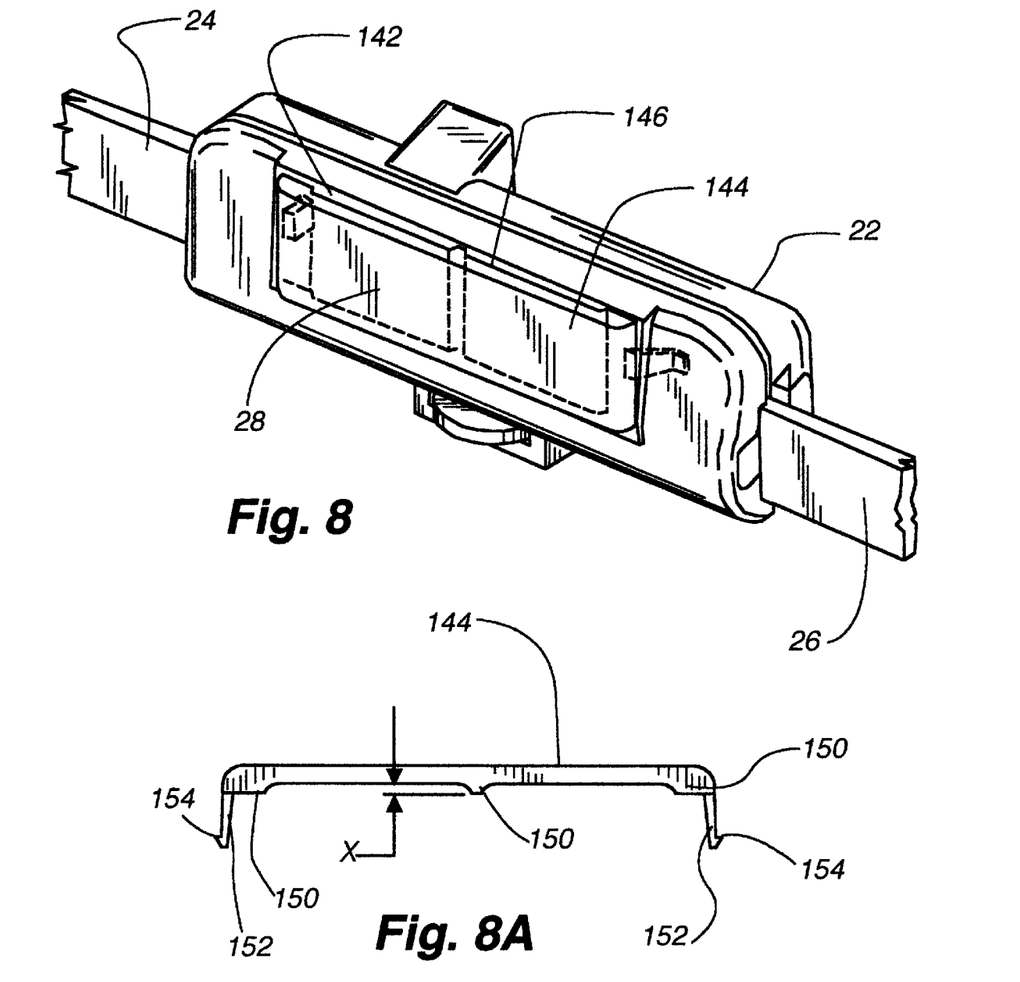
FIG. 8 is an enlarged partial view of the main body of the facebow of the present invention showing the sight structure.
FIG. 8A is a front view of the cover of the sight structure.
Figure 8B:
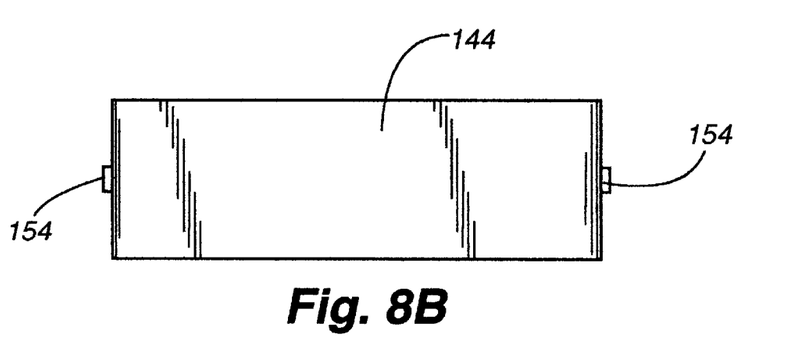
FIG. 8B is a top view of the cover of the sight structure.

The sight structure 28 of the present invention is a novel feature eliminating the need to use a pointer 34 to locate the third arbitrary reference point 40 marked on the patient's face. See FIGS. 7, 8, 8A and 8B. The sight structure 28 is defined by the top surface 142 of the main body of the facebow and a sight cover 144. The sight cover 144, when mounted on the main body 22, defines a gap 146 between the cover 144 and the top surface 142 of the main body, this gap 146 being the sight through which the dental professional views the patient's face. The critical dimensions of the sight include that the gap be approximately 0.040 inches at the point closest the user's face (see height dimension X, FIG. 8A), or along the interior edge 148 of the sight cover 142. The gap 146 along the exterior edge of the sight cover, or closest to the rear surface of the main body, is relatively immaterial. Another important parameter is that the sight be positioned at an angle α of preferably 7.5 degrees downward of the horizontal, measured from the middle of the gap, as shown by angle α in FIG. 7. Based on an assumption that the front of the face is approximately 3.2 inches from the external auditory meatus, these critical dimensions provide a tolerance of approximately ±2 degrees from horizontal when locating the third arbitrary reference mark 40. While a range of view of ±2 degrees from horizontal is not as accurate as using the pointer 34, the use of the sight structure 28 is faster, less intrusive and more comfortable for the patient. The ±2 degrees tolerance from horizontal also provides adequate precision for obtaining the proper orientation of the bite molds in the dental articulator.

The sight cover 144 is generally an elongated member having support legs 150 extending downwardly from either end, and from the middle. When the sight cover 144 is mounted on the main body, these three support legs 150 rest on the top 142 of the main body 22 to help keep the dimensions of the gap from deforming under load or after many uses. An anchor leg 152 extends downwardly from the two end support legs, and each is received in a corresponding slot formed in the top surface 142 of the main body 22. Each anchor leg 152 has a hook 154 formed on its end which securely attaches the sight cover 144 to the top surface 142 of the main body 22 in a simple and efficient manner. The hooks 154 keep the sight cover 144 from being easily removed from the main body 22 once attached thereto. However, it is contemplated that different sight covers 144 having different gaps can be placed on the same main body 22. It is also contemplated that different structures can be used to securely affix the sight cover 144 to the main body. The gap dimension is defined by the length of the support legs 150. Preferably, the sight cover is approximately 0.750 inches wide. This dimension, along with the height of the gap, provides the preferable range of view for locating the third reference point. See FIGS. 8A and 8B.

The facebow was designed such that the entire device can be autoclaved, or the ear pieces can be easily removed and autoclaved separately. The facebow 20 and ear pieces 32 are designed specifically for steam autoclaves, chemical vapor autoclaves, and cold sterilization. Since the high temperature of autoclave processing prohibits the use of a lubricant to obtain smooth operation of the facebow arms, the bearing plate 108 is used between the arms 24 and 26 to provide for lubrication. The plate 108 not only provides lubrication but aids assembly by eliminating the problems associated with applying lubricant, e.g., applying the correct amount, eliminating the mess, and reducing the effect of uneven surfaces on the arms, etc.

The assembly of the facebow 20 proceeds as described below. The gear racks 76 and 94 are attached to the arms 24 and 26, respectively, with flat head screws. One of the arms, such as left arm 24, is laser etched with the intercondylar distance scale. The scale is positioned from the end of the slot contained within the arm. The laser etched arm 24 is placed in its mating slot 106 in the lower portion 102 of the main body 22 and positioned in the extended position. This is the datum in which the scale was positioned. The pinion gear 80 is placed in the yokes 110 to mesh with the gear rack 76 on the lower arm 24. The bearing plate 108 and cam lock 30 are then placed into the lower portion 102 of the main body 22. The other arm 26 has the gear rack 94 attached as noted above, and is placed on the lower portion 102 of the main body 22 in the extended position. The top portion 100 of the main body 22 is then positioned over these parts such that the bosses from one of the main body portions aligns with the counter bores in the other of the main body portions, and screws are used to secure the top and bottom main body portions together. The sight cover 144 is then snapped into position, as described above. The ear pieces 32 are then attached to the arms.

In operation, the arbitrary third point of reference 40 is found by marking a point approximately 43 millimeters superior of the lateral incisor edge on the face with a referenced plane locator. The bite fork assembly is affixed with the bite registration material (mold material) in the patient's mouth, and the transfer jig assembly is attached to the bite fork for taking a facebow measurement. A threaded set screw is used to hold the transfer jig assembly to the bite fork.

The facebow 20 is then moved to its extended position to allow clearance for the face. The arms 24 and 26 are moved inwardly towards one another to close the facebow such that the ear pieces 32 are seated securely in the patient's ears. The design of the ear pieces 32 eliminates the need to pull forward on the facebow. See FIG. 3. The facebow 20 is then locked in position with the cam lock 30. The facebow is aligned with the arbitrary third point of reference 40 by pivoting the facebow through a vertical arc in front of the patient's face such that the mark is centered within the gap 146 created by the sight structure 128 (centered top to bottom in the gap). This step can also be accomplished by positioning the attached pointer 34 so it aligns with the arbitrary third reference point 40. The intercondylar distance is read from the scale formed on the facebow 20 and recorded if necessary. The facebow 20 is then affixed to the transfer jig. After removing the entire assembly, the transfer jig is removed from the facebow to mount the cast onto an articulator (casts must be made from the molds first, as is known in the art). The facebow is now able to be used again, and if desired either the ear pieces can be removed and sterilized or the entire facebow can be sterilized.

While the invention has been particularly shown and described with reference to a preferred embodiment thereof, it will be understood by those skilled in the art that various other changes in the form and details may be made without departing from the spirit and scope of the invention.

I claim:

1. A facebow for registering the position of a third reference point on a patient's face, said facebow comprising:
    a left arm,
    a right arm;
    a main body adjustably receiving said left and right arms; and
    a sight structure formed on said housing for use in locating the third reference point.

2. A facebow as defined in claim 1, wherein:
    said sight structure includes a gap having a height dimension to create a desired range of view.

3. A facebow as defined in claim 2, wherein:
    said gap forms left and right sides.

4. A facebow as defined in claim 2, wherein said range of view is approximately 4 degrees.

5. A facebow as defined in claim 2, wherein said gap is nominally approximately at least 0.040 inches high.

6. A facebow as defined in claim 2, wherein said gap is nominally approximately no greater than 0.040 inches.

7. A facebow as defined in claim 2, wherein said gap is nominally approximately 0.040 inches high and the cover is approximately 0.750 inches wide.

8. A facebow as defined in claim 1, wherein said sight structure further comprises:
    a cover mounted on said main body to form said gap between said cover and said main body.

9. A facebow as defined in claim 8, wherein said cover is removably attached to said main body.

10. A facebow as defined in claim 8, wherein:
    said cover includes an elongated member and at least two legs, one at each end of said member;
    said legs engaging said cover to space said member from said main body to form said gap.

11. A facebow as defined in claim 1, wherein said entire facebow is sterilizable.

12. A method of using a facebow on a patient's face, including ears, having a reference point thereon, to properly orient a bite fork, adustably engaged with said facebow, with respect to the patient's face, said method including the steps of:
    providing a main body and left and right arms on the facebow and engaging the left and right arms with the respective ears of the patient,
    providing a sight structure on said facebow and viewing the patient's face through the sight to locate the reference point; and securing the main body to the bite fork to register the relative position of the bite fork to the facebow.

13. A facebow for engaging a patient's head to register the position of a bite fork in a patient's mouth, said facebow comprising:

a main body;

a left arm slidably positioned in said main body;

a right arm slidably positioned in said main body, a rack and pinion assembly positioned in said main body and operably engaging said left and right arms to cause said right arm and said left arm to move in opposite directions from one another upon movement of one arm, respectively, said rack and pinion assembly comprising:

a rack attached to each arm, one of said racks facing downwardly, and one of said racks facing upwardly, said racks facing each other;

a pinion gear rotatably fixed in said main body on a horizontal axis of rotation and engaging both of said racks; wherein movement of one of said left and right arms with respect to said main body causes the other of said left and right arms to move in the opposite direction.

14. A facebow as defined in claim 13, further comprising: a sight structure formed on said main body to align the facebow relative to the patient's face.

15. A facebow as defined in claim 13, wherein:

said main body defines an upper and lower slots;

said left arm being received in said lower slot, said right arm being received in said upper slot;

said pinion gear being positioned between said right and left arms.

16. A facebow as defined in claim 15, wherein:

a bearing plate is positioned between said right and left arms to act as a bearing surface during the movement of said left and right arms.

17. The facebow as defined in claim 15, further comprising:

a lock knob positioned in said main body and being selectively engaged with said left and right arms to fix the position of said right and left arms with respect to said main body.

18. A facebow as defined in claim 17, wherein:

said lock knob is oriented in said main body about a horizontal axis of rotation, defines a cam surface that engages said main body, and can be rotated to cause said cam surface to engage said main housing and move axially toward said left and right arms to engage said left and right arms, and away from said left and right arms.

19. A facebow for engaging a patient's head to register the position of a bite fork in a patient's mouth, said facebow comprising:

a main body;

a left arm slidably positioned in said main body;

a right arm slidably positioned in said main body;

an ear piece positioned on each of said left and right arms, each of said ear pieces comprising:

a body portion having a front side, a back side, a terminal end and a receiving end;

a slot formed in said back side for receiving said one of said left and right arms;

said front face at said terminal end forming a bulbous lobe.

20. A facebow as defined in claim 19, wherein said receiving end has a generally conical shape.

21. A facebow as defined in claim 19, wherein said arm is flush with said back side of said ear piece when mounted on said arm.

22. An ear piece for use on a facebow having an arm, said ear piece comprising:

a body portion having a front side, a back side, a terminal end and a receiving end;

a slot formed in said back side for receiving said arm;

said front face at said terminal end forming a bulbous lobe.

23. An ear piece as defined in claim 22, wherein said receiving end has a generally conical shape.

* * * * *

UNITED STATES PATENT AND TRADEMARK OFFICE
CERTIFICATE OF CORRECTION

PATENT NO. : 6,152,732
DATED : November 28, 2000
INVENTOR(S) : Eric Lindekugel

It is certified that error appears in the above-identified patent and that said Letters Patent is hereby corrected as shown below:

Drawings,
Sheet 4 of 10, add reference numbers -- 110, 106, 104 --
Sheet 4 of 10, "76" on the right side of the page should be -- 77 --
Sheet 6 of 10, "76" should be -- 77 --
Sheet 6 of 10, "98" should be -- 99 --
Sheet 9 of 10, add reference number -- 108 -- to Fig. 7
Sheet 9 of 10, "76" should be -- 77 -- in Fig. 7

Column 7,
Line 30, "gear rack 76" should be -- bottom gear rack 77 -- (2 places)
Line 35, "gear rack 76" should be -- bottom gear rack 77 --
Lines 37-38, "gear rack 76" should be -- bottom gear rack 77 --
Line 40, "rack 76" should be -- bottom gear rack 77 --
Line 41, after "apertures" add -- 84, 86 --
Line 42, "gear rack 76" should be -- bottom gear rack 77 --
Line 47, "The gear" should be -- A top gear --
Line 47, "side" should be -- surface --
Line 48, "gear" should be -- top gear --
Line 55, "98" should be -- 99 --

Column 8,
Line 9, "gear rack 76" should be -- bottom gear rack 77 --
Line 16, "the rack" should be -- the top gear rack --
Line 29, "bottom rack 76" should be -- bottom gear rack 77 --
Lines 30 and 32, "top rack" should be -- top gear rack --
Line 33, "bottom rack 76" should be -- bottom gear rack 77 --
Line 37, after "members" add -- 110, 116 --
Line 40, "98" should be -- 99 --
Line 45, "pinion gear" should be -- pinion gear 80 -- (2 places)
Line 46, "rack" should be -- top gear rack --
Line 47, "top rack" should be -- top gear rack --
Line 50, "bottom racks" should be -- bottom gear racks 94, 77 --
Line 65, "gear system" should be -- pinion gear system 99 --
Lines 66-67, "the racks 76" should be -- the bottom and top gear racks 77 --

UNITED STATES PATENT AND TRADEMARK OFFICE
CERTIFICATE OF CORRECTION

PATENT NO.    : 6,152,732
DATED         : November 28, 2000
INVENTOR(S)   : Eric Lindekugel It is certified that error appears in the above-identified patent and that said Letters Patent is hereby corrected as shown below:

Column 9,
Line 1, "the racks" should be -- the bottom and top gear racks 77, 94 --
Line 12, after "system" add -- 99 --
Line 13, "gear rack" should be -- bottom and top gear racks 77, 94 --
Line 15, "gear rack 76" should be -- bottom or top gear rack 77 --
Lines 16-17, "the gear rack." should be -- the bottom or top gear rack 77, 94. --

Column 11
Line 31, "gear racks 76" should be -- bottom and top gear racks 77 --
Lines 39-40, "the gear rack 76" should be -- the bottom gear rack 77 --
Line 40, "lower arm" should be -- lower left arm --
Line 42, "the gear" should be -- the top gear --

Column 12,
Line 28, "said housing" should be -- said main body --
Line 41, "2" should be -- 8 --
Line 44, "1" should be -- 2 --

Column 14,
Line 7, "housing" should be -- body --
Line 23, "face" should be -- side --
Line 27, "said arm" should be -- one of said left and right arms --
Line 28, "on said arm." should be -- on said one of said left and right arms. --

Signed and Sealed this

Thirteenth Day of January, 2004

JON W. DUDAS
*Acting Director of the United States Patent and Trademark Office*